(12) United States Patent
Gritsenko et al.

(10) Patent No.: US 6,377,840 B1
(45) Date of Patent: Apr. 23, 2002

(54) SIGNAL ACQUISITION AND PROCESSING SYSTEM FOR REDUCED OUTPUT SIGNAL DRIFT IN A SPECTROPHOTOMETRIC INSTRUMENT

(75) Inventors: Sergey I. Gritsenko; Mark S. Lewandowski, both of Hutchinson; Dean E. Myers, Stewart, all of MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 0 days.

(21) Appl. No.: 09/585,089

(22) Filed: Jun. 1, 2000

Related U.S. Application Data

(60) Provisional application No. 60/137,381, filed on Jun. 3, 1999, provisional application No. 60/137,390, filed on Jun. 3, 1999, provisional application No. 60/137,383, filed on Jun. 3, 1999, provisional application No. 60/137,305, filed on Jun. 3, 1999, and provisional application No. 60/137,382, filed on Jun. 3, 1999.

(51) Int. Cl.[7] .................................................. A61B 5/05
(52) U.S. Cl. ........................ 600/476; 356/319; 356/326; 356/320; 356/477
(58) Field of Search ................................. 600/309, 300, 600/473, 310, 342, 476; 606/2, 13, 14, 15, 16, 17, 18; 607/1, 88, 91–93; 356/73.1, 477, 319–326; 358/319–330, 432, 433, 226, 229, 230; 359/237–388; 250/330, 336.1, 338.1, 339.06–339.08, 345–370

(56) References Cited

U.S. PATENT DOCUMENTS

| | | |
|---|---|---|
| 3,874,781 A | 4/1975 | Thiel |
| 4,176,958 A | 12/1979 | Way et al. |

(List continued on next page.)

FOREIGN PATENT DOCUMENTS

| | | |
|---|---|---|
| DE | 44 46 721 A1 | 2/1996 |
| EP | 0 476 596 A1 | 3/1992 |
| EP | 0 800 099 A2 | 10/1997 |
| EP | 0 816 829 A2 | 1/1998 |
| EP | 0 868 881 A1 | 10/1998 |

OTHER PUBLICATIONS

Automatic Drift Compensating Circuit For Digital Spectrophotometer document.
Reiter, et al., *A Long Term Stable Reference Light Source Using LEDS For Stabilization Of Scintillation Spectrometers* Nuclear Instruments and Methods 173 (1980) 275–282.

(List continued on next page.)

*Primary Examiner*—Marvin M. Lateef
*Assistant Examiner*—Jeoyuh Lin
(74) *Attorney, Agent, or Firm*—Faegre & Benson LLP

(57) ABSTRACT

A spectrophotometric instrument including a source of measurement light signals having measurement light wavelengths, and a probe having a tissue-engaging surface, a plurality of send fibers coupled to the measurement light signal source for transmitting the measurement light signals to the tissue-engaging surface, and a plurality of receive fibers for receiving light including the measurement light signals after the measurement light has been transmitted through the tissue. The instrument also has reference signal optics coupled to the measurement light signal between the measurement light signal source and the tissue-engaging surface for transmitting a reference light signal portion of the measurement light signal, a detector for generating electrical signals representative of the measurement light signals and the reference light signals, optical paths for coupling the measurement light signal from the receive fibers and the reference light signal portion from the reference signal optics to the detector, and an optical path control for selectively allowing either the measurement light signal portion or the reference light signal portion to the detector. The optical path control enables the detector to output a reference light sample value when the reference light signal portion is coupled to the detector, and to output a measurement light sample value when the measurement light signal portion is coupled to the detector.

15 Claims, 11 Drawing Sheets

U.S. PATENT DOCUMENTS

| | | | |
|---|---|---|---|
| 4,257,709 A | | 3/1981 | Mostyn, Jr. |
| 4,327,964 A | | 5/1982 | Haesly et al. |
| 4,427,879 A | | 1/1984 | Becher et al. |
| 4,661,693 A | | 4/1987 | Masanbu |
| 4,684,245 A | | 8/1987 | Goldring |
| 4,798,440 A | | 1/1989 | Hoffer et al. |
| 4,910,539 A | | 3/1990 | Mathis et al. |
| 4,998,973 A | | 3/1991 | Kikuchi |
| 5,039,224 A | | 8/1991 | O'Rourke et al. |
| 5,040,889 A | | 8/1991 | Keane |
| 5,140,663 A | | 8/1992 | Edwards et al. |
| 5,157,250 A | | 10/1992 | Oikari et al. |
| 5,212,748 A | | 5/1993 | Curtiss et al. |
| 5,224,186 A | | 6/1993 | Kishimoto et al. |
| 5,224,478 A | | 7/1993 | Sakai et al. |
| 5,297,227 A | | 3/1994 | Brown et al. |
| 5,304,173 A | * | 4/1994 | Kittrrell et al. ............... 606/15 |
| 5,339,375 A | | 8/1994 | Kerns |
| 5,456,251 A | | 10/1995 | Fiddian-Green |
| 5,460,182 A | * | 10/1995 | Goodman et al. .......... 128/664 |
| 5,477,853 A | | 12/1995 | Farkas et al. |
| 5,481,634 A | | 1/1996 | Anderson et al. |
| 5,584,296 A | | 12/1996 | Cui et al. |
| 5,719,977 A | | 2/1998 | Lampert et al. |
| 5,774,213 A | * | 6/1998 | Trebino et al. ............. 356/320 |
| 5,792,049 A | | 8/1998 | Eppstein et al. |
| 5,879,294 A | | 3/1999 | Anderson et al. |
| 5,896,485 A | | 4/1999 | Kirby |
| 5,902,246 A | | 5/1999 | McHenry et al. |
| 5,923,805 A | | 7/1999 | Anderson et al. |
| 6,049,762 A | * | 4/2000 | Ganz et al. ................. 702/104 |
| 6,058,324 A | * | 5/2000 | Chance ....................... 600/473 |
| 6,104,939 A | * | 8/2000 | Groner et al. .............. 600/322 |

OTHER PUBLICATIONS

Mangoyanov, *Stabilization System For Multidetector Scintillation Spectrometer*, Joint Institute for Nuclear Research, Dubna. Translated from Pribory i Tekhnika Éksperimenta, No. 2, pp. 76–81, Mar.–Apr. 1969.

Aleksanyan et al., *Stabilization and Calibration of Hodoscopic Serenkov Spectrometer*, Instruments and Experimental Techniques, vol. 30 No. 4, Part 1, Jul.–Aug. 1987, 793–797, Translated from Pribory i Tekhnika Éksperimenta, No. 4, pp. 40–43, Jul.–Aug. 1987.

INVOS® 3100A Cerebral Oximeter Specifications, Somanetics Corporation (1 page) Somanetics® 4100–SSA SomaSensor® (1 page).

NIRO 300, Continuous, non–invasive measurement of tissue oxygenation using light, Hamamatsu Photonics K. K., Japan (4 pages).

Plastazote®, Crosslinked LD polyethylene Foam, LD–2 (1 page).

International Search Report, PCT/US00/15175, mailed 19/09/2000, (4 pages).

International Search Report, PCT/US00/15175, mailed 26/02/2001, (5 pages).

International Search Report, PCT/US00/15174, mailed 19/09/2000, (5 pages).

International Search Report, PCT/US00/15075, mailed 22/09/2000, (4 pages).

International Search Report, PCT/US00/40086, mailed 22/08/2000, (5 pages).

* cited by examiner

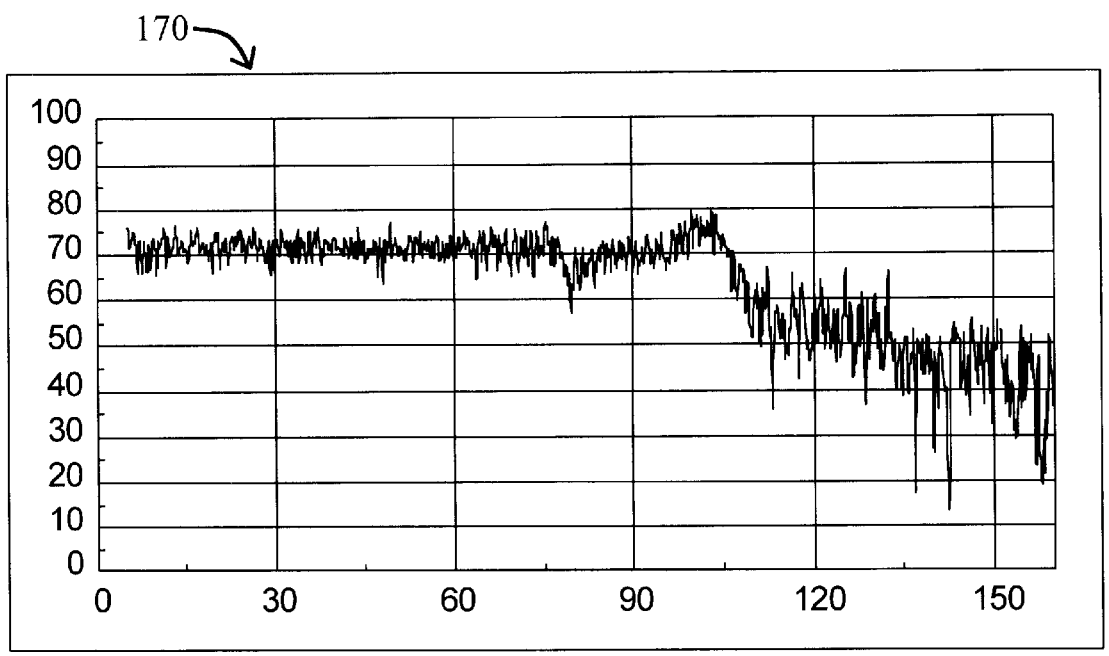
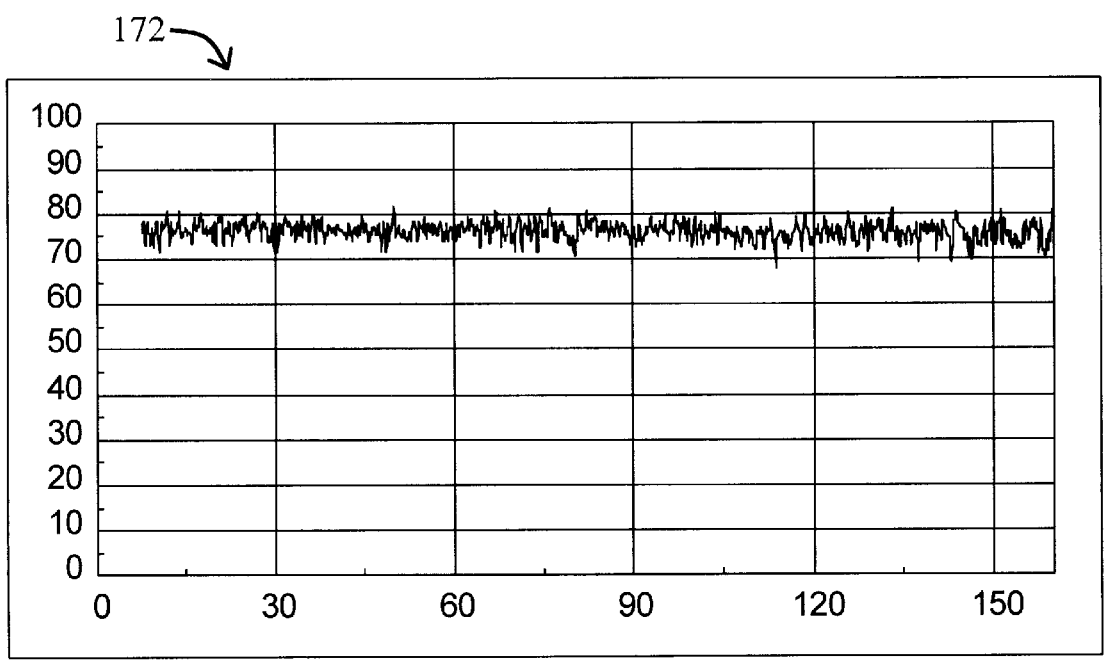
Figure 7

SIGNAL ACQUISITION AND PROCESSING SYSTEM FOR REDUCED OUTPUT SIGNAL DRIFT IN A SPECTROPHOTOMETRIC INSTRUMENT

REFERENCE TO RELATED APPLICATIONS

1. This application claims the benefit of the following U.S. Provisional Patent Applications
    i) Ser. No. 60/137,381 filed on Jun. 3, 1999 and entitled "Signal Acquisition And Processing System For Reduced Output Signal Drift In A Spectrophotometric Instrument;
    ii) Ser. No. 60/137,390 filed on Jun. 3, 1999 and entitled "Fiber Optic Light Mixer;" and
    iii) Ser. No. 60/137,383 filed on Jun. 3, 1999 and entitled "Disposable Tissue Probe Tip;"
    iv) Ser. No. 60/137,305 filed on Jun. 3, 1999 and entitled "Optical Connector Latching Mechanism For A Spectrophotometric Instrument;" and
    v) Ser. No. 60/137,382 filed on Jun. 3, 1999 and entitled "Calibration Mode Recognition And Calibration Algorithm For Spectrophotometric Instrument."

2. Reference is hereby made to the following commonly assigned and copending U.S. Patent Applications which are incorporated herein by reference:
    i) Ser. No. 09/585,144 filed on Jun. 1, 2000 and entitled "Fiber Optic Light Mixer;"
    ii) Ser. No. 09/584,862 filed on Jun. 1, 2000 and entitled "Disposable Tissue Probe Tip;"
    iii) Ser. No. 09/584,487 filed on Jun. 1, 2000 and entitled "Optical Connector Latching Mechanism For A Spectrophotometric Instrument;" and
    iv) Ser. No. 09/584,990 filed on Jun. 1, 2000 and entitled "Calibration Mode Recognition And Calibration Algorithm For Spectrophotometric Instrument."

FIELD OF THE INVENTION

The present invention relates generally to spectrophotometric instruments. In particular, the invention is an optical configuration and measurement signal acquisition and processing system for enhancing the output signal stability of a spectrophotometric instrument.

BACKGROUND OF THE INVENTION

Spectrophotometric-type instruments are known and used in a variety of applications. An instrument of this type is, for example, disclosed in the Anderson et al. U.S. Pat. No. 5,879,294. There remains, however, a continuing need for instruments capable of providing measurement to a higher degree of accuracy with relatively low levels of output signal drift.

BRIEF DESCRIPTION OF THE DRAWINGS

FIG. 7 is a pair of graphs illustrating uncompensated and compensated $StO_2$ signal drift over the same time conditions of the graphs of FIG. 6.

DETAILED DESCRIPTION OF THE PREFERRED EMBODIMENTS

Figure 1:
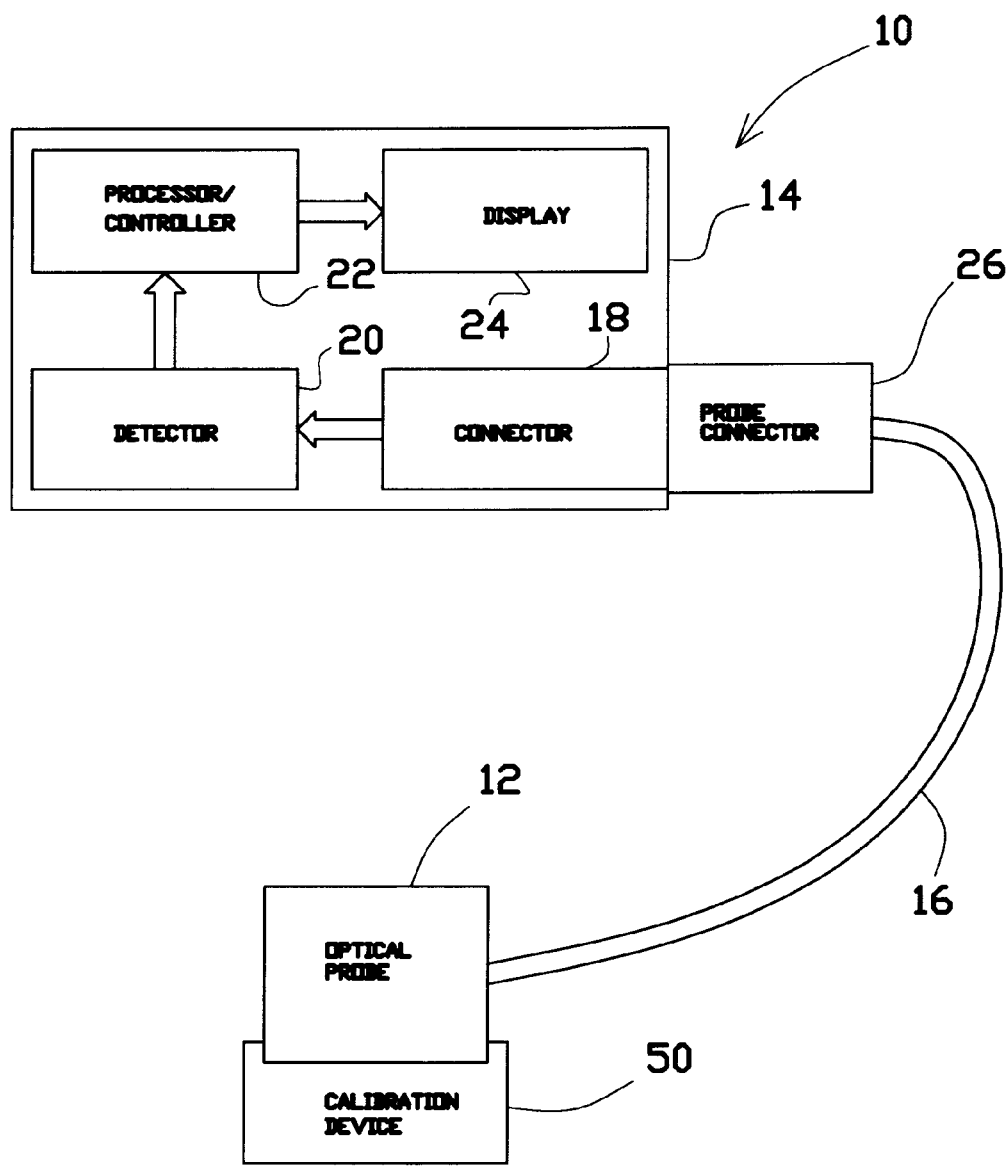
FIG. 1 is block diagram of an instrument useful in the practice of the present invention, along with a probe connector and optical probe connected by optical fibers and a calibration device.
Figure 2:
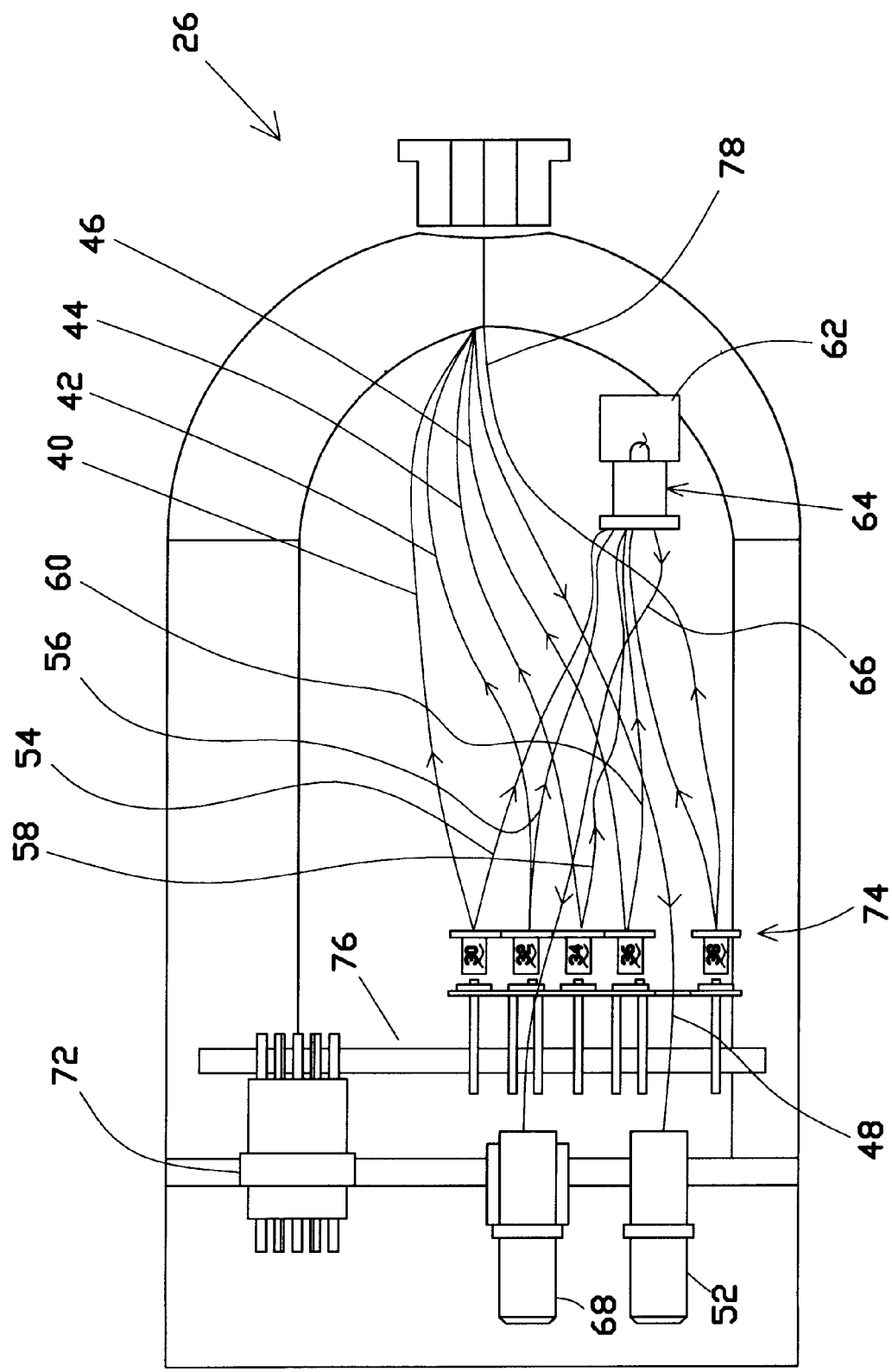
FIG. 2 is a detailed view of the probe connector shown in FIG. 1.

An instrument 10 in which the signal acquisition and processing system of the present invention can be incorporated is described generally with reference to FIGS. 1 and 2. As shown, the instrument 10 includes an optical probe 12 which is releasably connected to an electronics package 14 via optical fibers 16. The electronics package 14 includes a connector 18, a detector 20, a processor/controller 22, and a display 24. In operation, the probe 12 is positioned on the tissue to be measured or analyzed. The probe 12 is interfaced to the instrument electronics through the optical fibers 16 and a probe connector 26. The probe connector 26 includes light emitting diodes (LEDs) or other light sources 30, 32, 34, 36, and 38 for generating light at a number of different wavelengths (e.g., 800, 760, 720, 680, and 530 nm, respectively). The light used to measure the characteristics of the tissue is coupled to the probe by send optical fibers 40, 42, 44, and 46. After being transmitted from the tissue-engaging surface of the probe 12 into the tissue being measured, the light will travel through the tissue before being collected at the end of the receive optical fiber 48. This collected light (measurement light signal) is then transmitted to the instrument 14 through the probe connector 26 and electronics package connector 18. A reference light signal corresponding to each of the measurement light signals (i.e., the reference light signals are not transmitted through the tissue) is also transmitted to the electronics package connector 18. The optical probe 12 is described in greater detail in the above-referenced U.S. Patent Applications entitled "Disposable Tissue Probe Tip" and "Fiber Optic Light Mixer."

The collected measurement light signals and reference light signals received by the electronics package 14 are transmitted to the detector 20 which produces electrical signals representative of these light signals at each wavelength of interest. The processor/controller 22 then processes these signals to generate data representative of the measured tissue parameter (e.g., saturated oxygen level ($StO_2$)). The measurement reading can be visually displayed on the display 24. Algorithms used to compute the tissue parameter data are generally known and described in the Anderson et al. U.S. Pat. No. 5,879,294.

Calibration procedures are typically performed to enhance the accuracy of the measurements subsequently made by the instrument 14. Methods and devices for calibrating spectrophotometric-type instruments are generally known and disclosed in the Anderson et al. patent. The calibration can, for example, be performed by placing the probe 12 on a calibration device 50 such as that shown in FIG. 1. The calibration device 50 includes a housing which is filled with light scattering material. The light scattering material is generally spectrally flat (i.e., reflects all light to the same degree) to provide a reference spectrum. White polyethylene foam such as Plastazote LD45 available from Zotefoams plc. can be used for this purpose.

One configuration of a spectrophotometric instrument of the type described above includes, for each wavelength of interest, a photomultiplier tube (PMT) for detecting the measurement light signal, and a photodiode for detecting the calibration recognition signal (or ambient light). Thermal electric coolers can be included in the electronics package to help maintain temperature control of the optical bench to which the PMTs and photodiodes are mounted, and thereby reduce output signal drift.

The present invention is an optical bench configuration, measurement and reference signal acquisition system and measurement and reference signal processing algorithm which provide relatively low levels of output signal drift. The probe connector 26 used in connection with this invention is illustrated in FIG. 2, which shows an embodiment having a reference signal generated within the connector. As shown, the probe connector 26 includes 4 LED's 30, 32, 34, and 36 for generating the measurement light signals at 800, 760, 720 and 680 nm. Light signals from each of these LEDs are coupled to the probe 12 by a separate measurement signal send fiber 40, 42, 44, 46. After being transmitted through the tissue being analyzed and collected at the probe, the measurement light signal is coupled back to the probe connector by a measurement signal receive fiber 48. The end of the measurement signal receive fiber 48 terminates in the probe connector 26 at a sample ferrule 52 which is adapted to mate with a socket in the connector 18 of the electronics package 14. The optical probe 12 is described in greater detail in the above-referenced U.S. Patent Applications entitled "Disposable Tissue Probe Tip" and "Fiber Optic Light Mixer."

A reference light signal is also provided by the probe connector 26. The reference light signal includes a portion of the light from each of the LEDs, and has not been transmitted from the probe before being collected. In the embodiment shown in FIG. 2, the reference light signal is collected by reference light signal send optical fibers 54, 56, 58 and 60, which extend respectively from each measurement light signal source LED 30, 32, 34, 36 to a light mixer/attenuator 62 formed by scattering material attached to a reference fiber fixturing ferrule 64. The reference signal send fibers 54, 56, 58, 60 are collected in the fixturing ferrule 64 at the scattering material along with a reference signal receive fiber 66. The reference light received from each LED is mixed at the mixer 62 and transmitted through the reference signal receive fiber 66. The end of the reference signal receive fiber 66 terminates in the probe connector 26 at a reference ferrule 68 which is adapted to mate with a socket in the connector 18 of the electronics package 14. Since it is significantly attenuated when it is transmitted through the tissue, the intensity of the measurement light signal at the connector is much less than the intensity of the non-attenuated reference light signal (e.g., about 1 million times less). In order to match the reference and measurement signal magnitudes to enable detection with a similar photo multiplier tube gain, the reference signal is attenuated at the mixer 62. The reference signal attenuation is obtained by reflectance mode positioning the reference signal send fibers 54, 56, 58, 60 equidistant from the centrally located reference signal receive fiber 66. The concentration of scattering material (such as titanium dioxide from Aldrich, Milwaukee, Wis.) within an optically clear epoxy substrate (such as EpoTech 301 from Epoxy Technology, Billerica, Mass.) can be adjusted to provide the appropriate level of attenuation within the mixer 62. The probe connector 26 also preferably has a 14 pin electrical connector 72 and an optical fiber fixturing ferrule 74 for each of the LED's 30, 32, 34, 36, and 38, each of which are mounted in a PC board 76, along with connector 72. LED 38 is a calibration recognition signal LED connected to a calibration recognition send fiber 78. It is to be understood that the arrows on fibers 40, 42, 44, 46 are to indicate "to probe tip" while the arrows on fiber 48 are to indicate "from probe tip."

A connector latch mechanism (not shown) latches the sample ferrule 52 and reference ferrule 68 of the probe connector 26 to the corresponding sockets (not shown) of the connector 18 in the electronics package 14. The latch connector mechanism is described in greater detail in the above-referenced U.S. Patent Application entitled "Optical Connector Latch Mechanism for Spectrophotometric Instrument."

Figure 3:
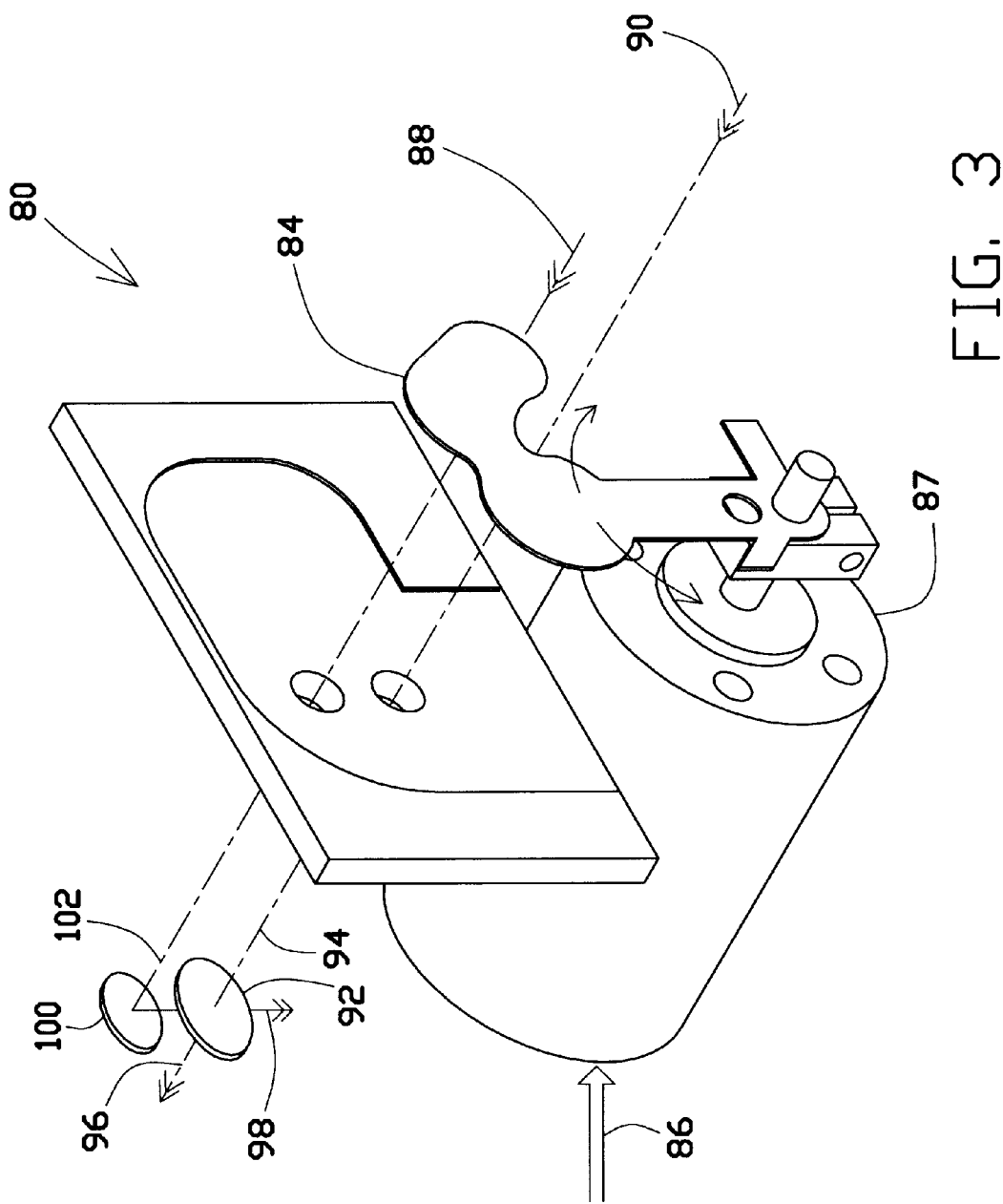
FIG. 3 is an isometric view of one embodiment of a shutter and path shifting optics useful in the practice of the present invention.

The reference light signal and measurement light signal (also referred to as a sample light signal) received at the connector at spatially separated paths are collimated by lenses or other optics and directed to a shutter and path-shifting optics 80 (FIG. 3). The shutter and path-shifting optics 80 selectively and alternately direct or fold the signals into a common path to the detector (optical bench). One embodiment of the shutter and path-shifting optics is illustrated in FIG. 3. As shown, a 30 degree stepper motor 82 drives opaque vane 84 and is controlled by the processor/controller 22, as indicated by arrow 86. The stepper motor 82 positions the vane 84 to selectively block one of the reference light signal and measurement light signal, and to transmit the other of signals to the path shifting optics. Arrow 88 indicates a collimated LED reference light path, while arrow 90 indicates a collimated measurement/sample light path (from the probe 12).

In the embodiment shown, the path shifting optics includes a 45° combining (beam splitting) mirror 92 in the measurement light path 94. This combining mirror allows a significant portion (e.g., 98–99%) of the measurement light signal to pass through the mirror to the detector 20 as indicated by arrow 96, with the remaining amount (e.g., 1–2%) being reflected away from the detector (i.e., trapped, as indicated by arrow 98). A 45° reflecting mirror 100 in the reference light path 102 reflects the reference light signal onto the side of the combining mirror opposite the side to which the measurement light signal is initially directed. A significant portion of the reference light signal will then pass through the combining mirror, while a smaller amount (e.g., 1–2%) will be reflected to the detector along the same optical path 96 as the measurement light signal. The measurement light signal and reference light signal are thereby directed or folded onto the same path 96 and directed to a common detector. In response to control signals from the processor/controller 22, the stepper motor 82 will position the opaque vane 84 to block one of the reference light signal or the measurement light signal. The other of the reference light signal and the measurement light signal will then be transmitted to the detector 20. This optics configuration also reduces the intensity of the reference light signal so it will not saturate the PMTs of the detector. Other mechanical and/or optics configurations can of course be used to provide these functions.

Figure 4:
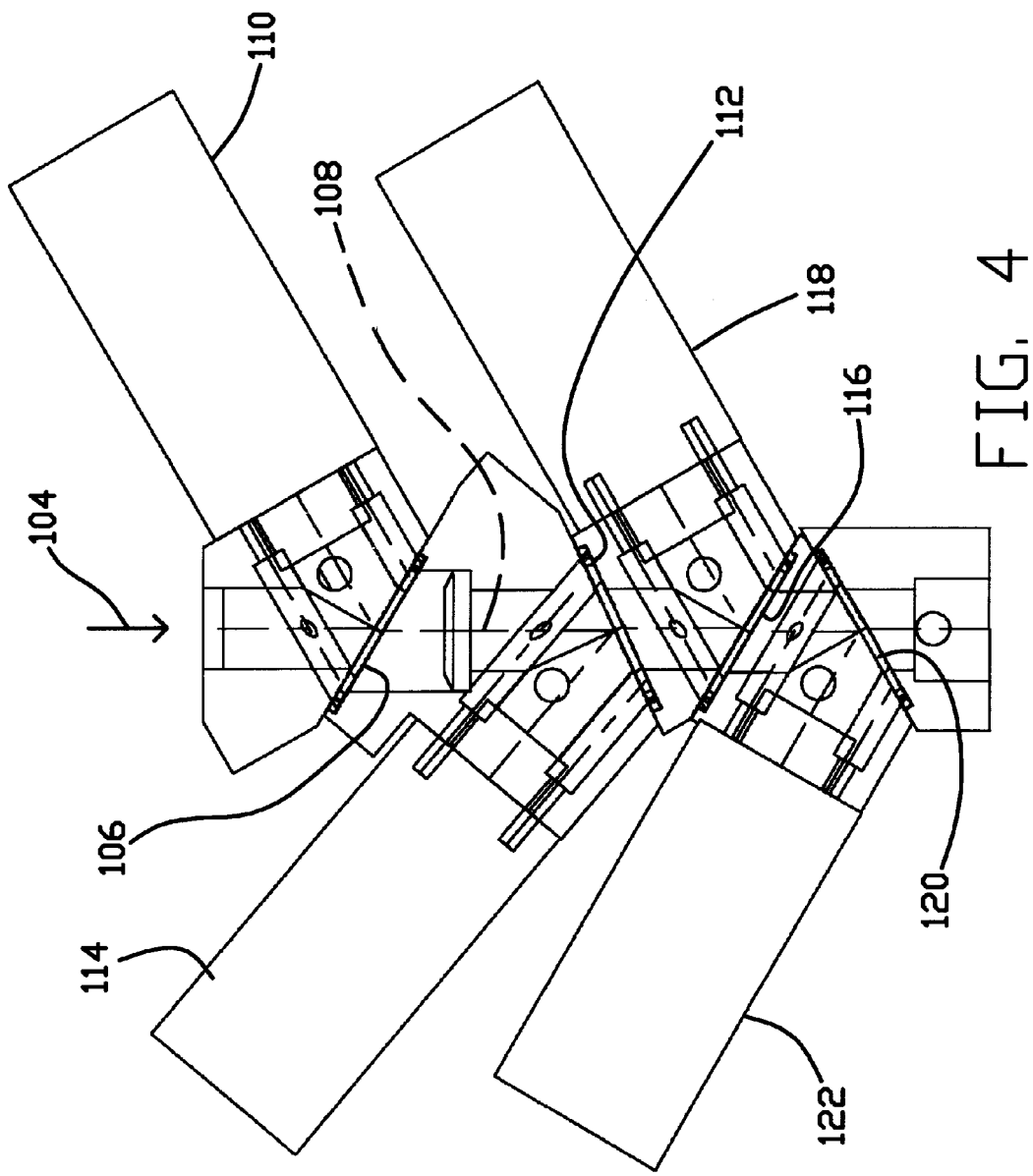
FIG. 4 is an illustration of a detector for use in the practice of the present invention.

FIG. 4 is an illustration of a detector 20 for use in the instrument 10 or electronics package 14 shown in FIG. 1 and described above. An approximate 5 mm diameter collimated light beam indicated by arrow 104 (either from the reference or sample (measurement) light signal) is transmitted to the front surface of an 800 nm dichroic mirror 106 which is positioned 30° from the optical axis 108. Approximately 90% of the light having a wavelength greater than 780 nm is reflected to the first photomultiplier tube (PMT) sensor 110 which has a 800 nm bandpass filter (+/−10 nm FWHM) positioned in front of the PMT sensor 110. Approximately 80% of the light having a wavelength shorter than 780 nm is transmitted through the 800 nm dichroic mirror 106 to the front surface of a 760 nm dichroic mirror 112 which is positioned 25° from the optical axis 108. Approximately 90% of the light having a wavelength greater than 740 nm is reflected to the second PMT sensor 114 which has a 760 nm bandpass filter (+/−10 nm FWHM) positioned in front of the PMT sensor 114. Approximately 80% of the light having a wavelength shorter than 740 nm is transmitted through the 760 nm dichroic mirror 112 to the front surface of a 720 nm dichroic mirror 116 which is positioned 30° from the optical axis 108. Approximately 90% of the light having a wavelength greater than 700 nm is reflected to the third PMT sensor 118 which has a 720 nm bandpass filter (+/−10 nm FWHM) positioned in front of the PMT sensor 118. Approximately 80% of the light having a wavelength shorter than 700 nm is transmitted through the 720 nm dichroic mirror 116 to the front surface of a 680 nm dichroic mirror 120 which is positioned 30° from the optical axis 108. Approximately 90% of the light having a wavelength greater than 660 nm is reflected to the fourth PMT sensor 122 which has a 680 nm bandpass filter (+/−10 nm FWHM) positioned in front of the PMT sensor 122. Approximately 80% of the light having a wavelength shorter than 660 nm is transmitted through the 680 nm dichroic mirror 120 to a detector block consisting of a 600 nm short pass filter (transmits light from approximately 400 nm to 600 nm) positioned in front of a photo diode detector. This detector is used to measure the presence of ambient light and/or the calibration material recognition signal (530 nm LED emitter). The calibration material recognition signal and the manner by which it is used is described in the above-referenced U.S. Patent Application entitled "Calibration Mode Recognition And Calibration Algorithm For Spectrophotometric Instrument."

During calibration procedures performed by the instrument, and for each of the PMTs used in connection with the calculation of the measurement (4 PMTs in the described embodiment), a baseline reading is established for both the measurement signal received from the probe (i.e., a baseline sample) and the reference signal (i.e., a baseline reference). These calibration measurement and reference baseline signals (for each PMT) are obtained through the use of the shutter and path-shifting optics 80 described above, and are stored in memory (not separately shown) and subsequently used in the measurement calculation algorithm.

As part of the measurement calculation algorithm, the processor/controller 22 calculates for each PMT a corrected sample (measurement) signal. The corrected sample signal is calculated as a function of the current sample (measurement) signal, the baseline reference signal and the current reference signal (taken at substantially the same time as the current sample signal) using the following formula:

Corrected Sample=Current Sample×Baseline Reference/Current Reference

In one embodiment the Current Sample is a 3 point running average of the live sampled PMT intensity values; the Baseline Reference is a 20 point block average of the LED signals just after a warm-up period; and the Current Reference is a 20 point running average of the live LED reference signals.

For each PMT, the processor/controller 22 calculates the tissue absorbance measurement as a function of the Baseline Sample and the Corrected Sample using the following formula:

Tissue Absorbance=Log (Baseline Sample/Corrected Sample)

In one embodiment, the Baseline Sample is a 20 point block average of the PMT intensity values just after the warm-up period (i.e., when the probe 12 is placed on the calibration device 50).

The optical bench configuration, measurement and reference signal acquisition system and measurement and reference signal processing algorithm described above compensate for and greatly reduce the drift of measurement readings made by the instrument. In effect, the instrument continuously switches the light detector between the measurement signal and the reference signal. The measurement signal traverses a complex electrical and optical path through the instrument and tissue being analyzed. The reference signal traverses substantially the same path with the exception of the tissue. Since many if not most of the signal distortion-causing factors such as thermal drift, aging and certain kinds of noise are common to both the measurement and reference signal paths, the processing system described herein causes these factors to cancel themselves. By comparing the two signals, a relatively clean and undistorted signal from the tissue can be acquired without the requirement of temperature control, component aging correction, noise reduction or other compensation approaches.

Figure 5:
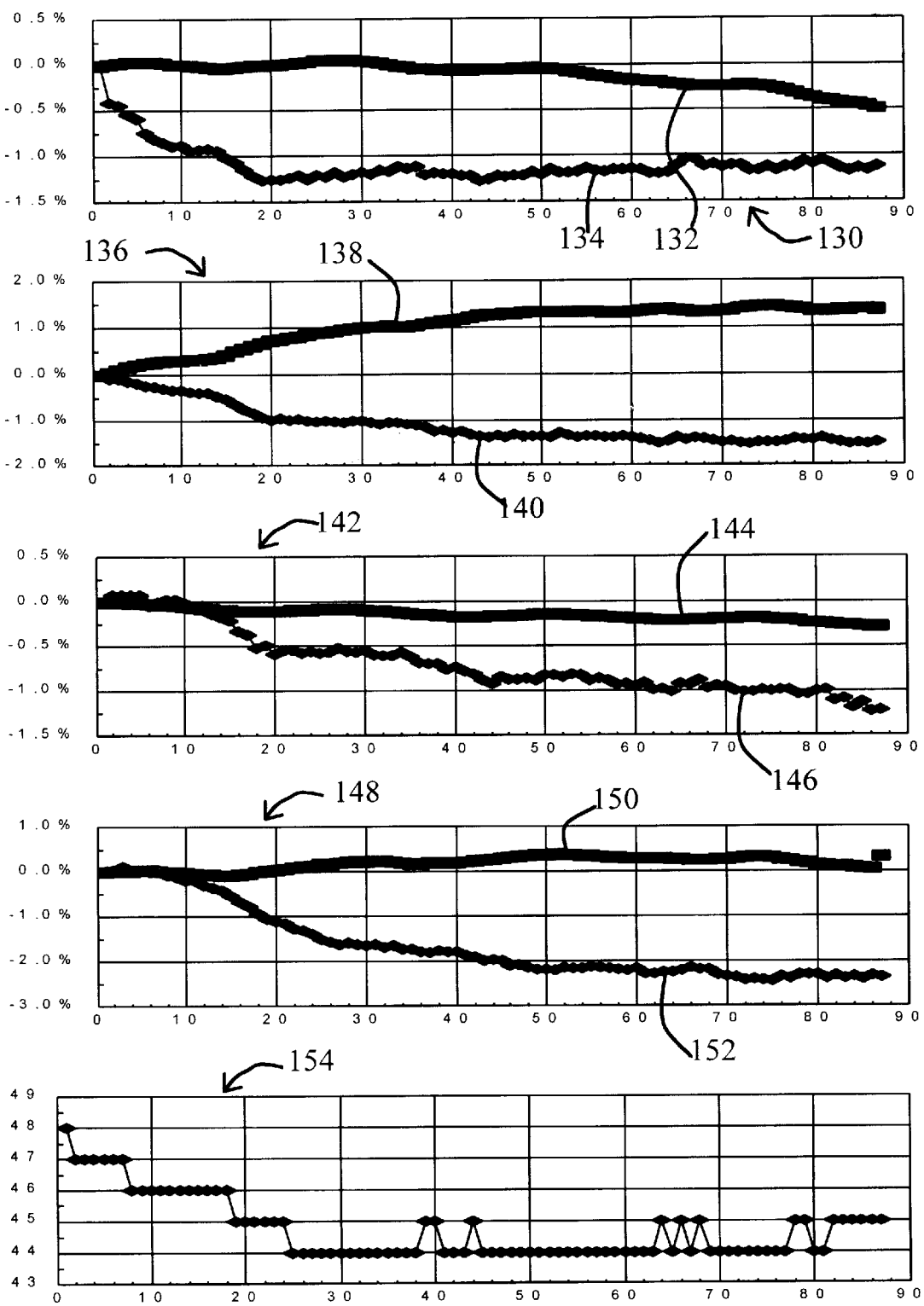
FIG. 5 is a set of graphs representing the characteristic drift for each channel for conventional (prior art) instrument.

Graph 1 (FIG. 5) is provided for purposes of comparison and represents the characteristic drift for each channel (i.e., set of LED reference signal photodiode (PD) and photomultiplier (PMT) measurement signal) for a spectrophotometric instrument (unlike the preferred embodiment described above) in which LED coupled photodiode detectors are used to measure and compensate for LED output intensity drift. Thermal control of the optical bench and regulation of the PMT control voltage (gain) are the approach used to stabilize sensitivity of each PMT detector in this instrument. For each channel the % change in signal intensity over time is plotted for both the LED feedback photodiode PD and the PMT.

Plot 130 shows mean signal drift for the 680 nm channel (n=1200) with % change in signal on the ordinate and time in hours on the abscissa with PD 680 data points indicated by squares 132, and PMT 680 data points indicated by diamonds 134.

Plot 136 shows mean signal drift for the 720 nm channel (n=1200) with % change in signal on the ordinate and time in hours on the abscissa with PD 720 data points indicated by squares 138, and PMT 720 data points indicated by diamonds 140.

Plot 142 shows mean signal drift for the 760 nm channel (n=1200) with % change in signal on the ordinate and time in hours on the abscissa with PD 760 data points indicated by squares 144, and PMT 760 data points indicated by diamonds 146

Plot 148 shows mean signal drift for the 800 nm channel (n=1200) with % change in signal on the ordinate and time in hours on the abscissa with PD 800 data points indicated by squares 150 and PMT 800 data points indicated by diamonds 152.

For each channel the LED feedback signal does not correlate with the PMT signal drift. This characteristic invalidates the use of the photodiode signals as a useful approach for correcting for overall signal drift. The drift on each PMT channel is an additive combination of both the LED output signal and PMT sensitivity (gain) drift.

Plot 154 shows mean $StO_2$ drift (n=1200) with % $StO_2$ on the ordinate and time in hours on the abscissa. The plot of calculated and simulated saturated oxygen (i.e., $StO_2$, a parameter measured by the instrument) shows that the instrument drifted –4% units over the first 25 hours.

Graph 2 (FIG. 6) illustrates signal drift trends for the preferred embodiment instrument described above. Every three seconds the measurement was segregated into an actual LED reference signal having approximately 8 times more intensity than the actual probe sample signal.

Plot 160 shows the 680 nm signal drift for both reference and sample with % drift in counts on the ordinate and time in minutes on the abscissa.

Plot 162 shows the 720 nm signal drift for both reference and sample with % drift in counts on the ordinate and time in minutes on the abscissa.

Plot 164 shows the 760 nm signal drift for both reference and sample with % drift in counts on the ordinate and time in minutes on the abscissa.

Plot 166 shows the 800 nm signal drift for both reference and sample with % drift in counts on the ordinate and time in minutes on the abscissa.

Plot 168 shows optical bench temperature obtained during both reference and sample signal measurements with temperature in degrees C on the ordinate and time in minutes on the abscissa.

The results demonstrate that the PMT reference and measurement sample signals track each other over a relatively large range of temperature-induced drift.

Figure 6:
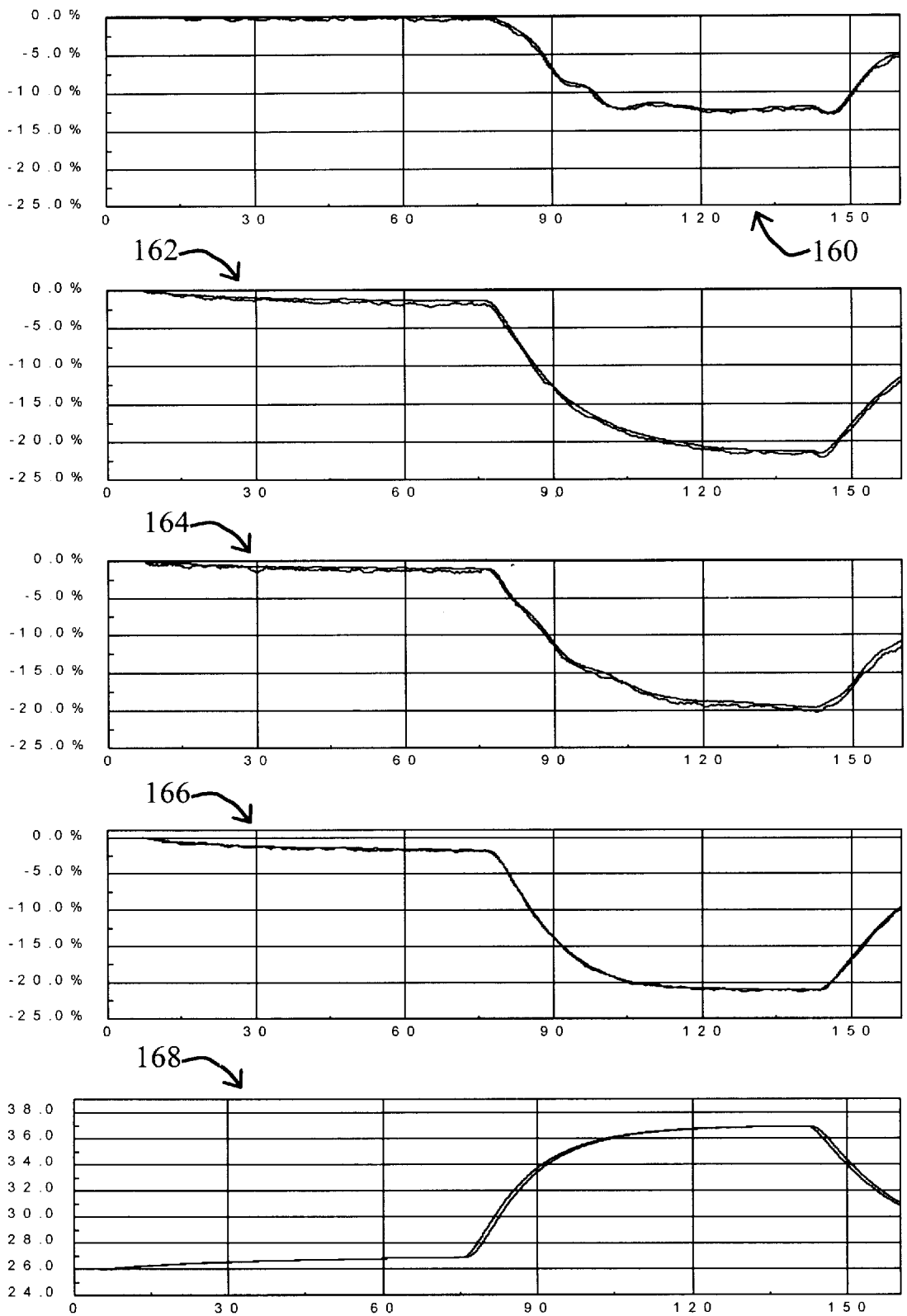
FIG. 6 is a set of graphs illustrating signal drift trends for an instrument according to the present invention.
Figure 8:
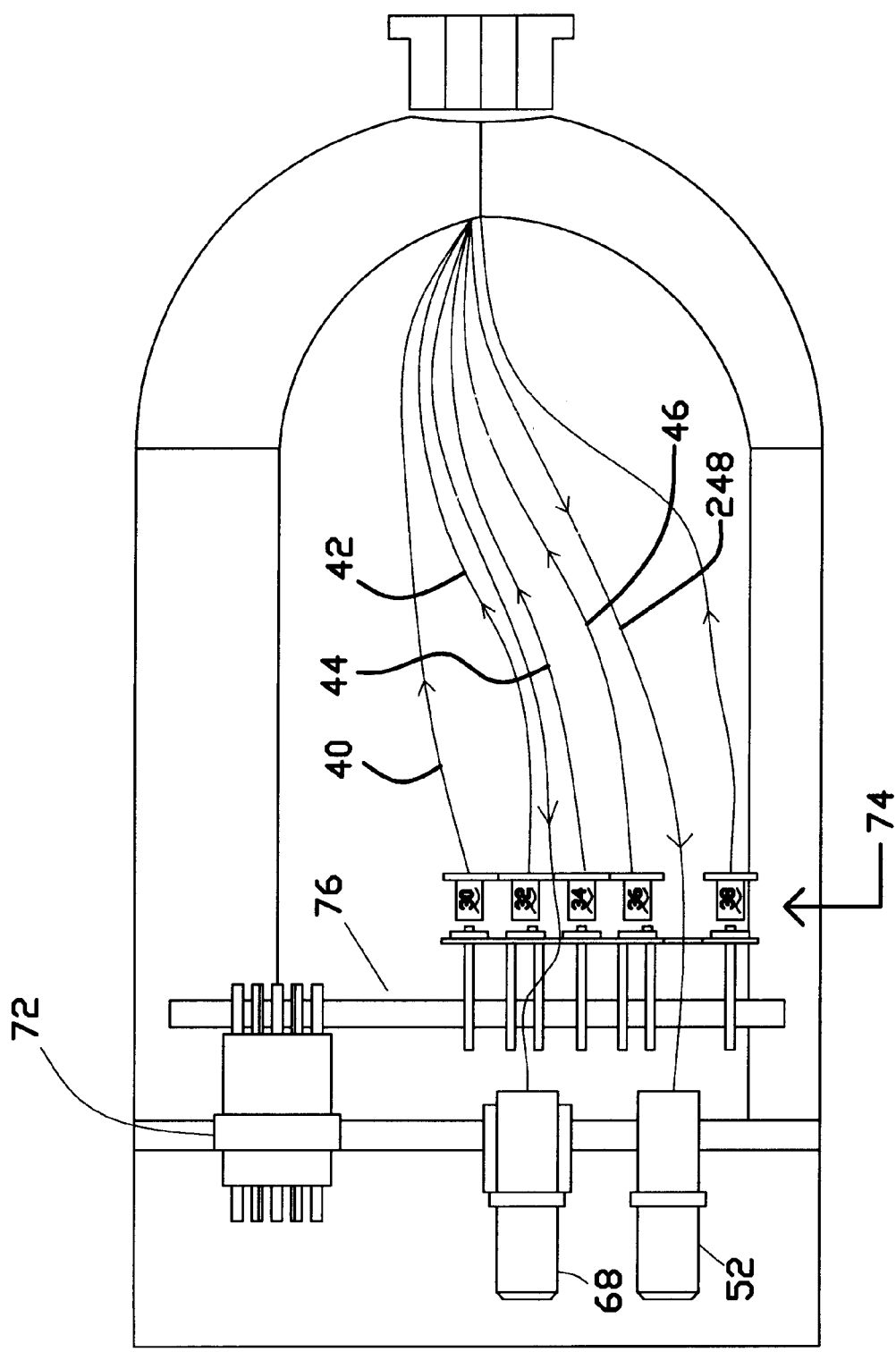
FIG. 8 is a view of an alternative embodiment of the probe connector of FIG. 2.

Graph 3 (FIG. 7) illustrates how the compensated and uncompensated $StO_2$ signals drifted during the same time conditions of the intensity drift trends shown in the second graph (FIG. 6).

Plot 170 shows % $StO_2$ drift with no drift compensation with % $StO_2$ drift on the ordinate and time in minutes on the abscissa.

Plot 172 shows % $StO_2$ drift with drift compensation with % $StO_2$ drift on the ordinate and time in minutes on the abscissa.

The drift corrected $StO_2$ signal in plot 172 of Graph 3 (FIG. 7) is calculated from 3 second PMT intensity values compensated in accordance with the formulas described above. Within the calculation the LED reference signal is time averaged longer than the sample signal in order to minimize the influence of noise on the reference signal measurement. It has been determined from tests of the optical bench temperature oscillations (period of approximately 3 minutes) that pulse width modulation control of the thermal electric coolers induced excessive noise within the compensated $StO_2$ signal. As long as the reference and sample signal track accurately it appears reasonable to let the PMT temperature float with ambient temperature in order to avoid excessive oscillation of the intensity values. It is evident from Graph 3 (FIG. 7) that the compensated $StO_2$ signal (with the thermal electric coolers removed) is more stable than the uncompensated signal and that the mean compensated $StO_2$ signal did not significantly drift when the live PMT signal intensities were forced to drift nearly 20% from the baseline values.

FIGS. 8–11 illustrate an alternative optical approach for obtaining the reference light signal. Rather than collecting the reference light signal from within the probe connector (i.e., there is no reference light from within the probe connector), a portion of the measurement light signal in the send fibers 40–46 (before it reaches the probe tip), is reflected back to (i.e., is intercepted by) a reference receive fiber 248 by a reflector. Several reflector options are shown.

Figure 9:
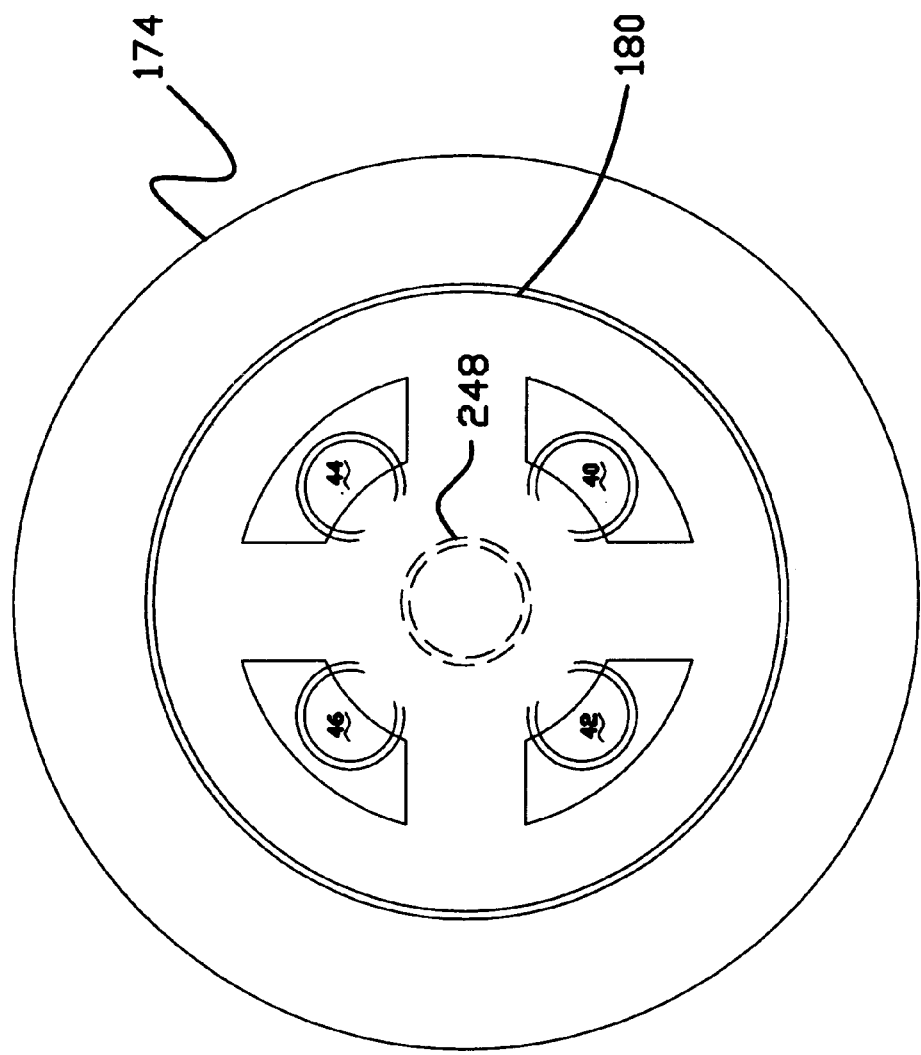
FIG. 9 is a view of a first alternative reflector plate for probe tip optical fibers useful in the practice of the present invention.
Figure 10:
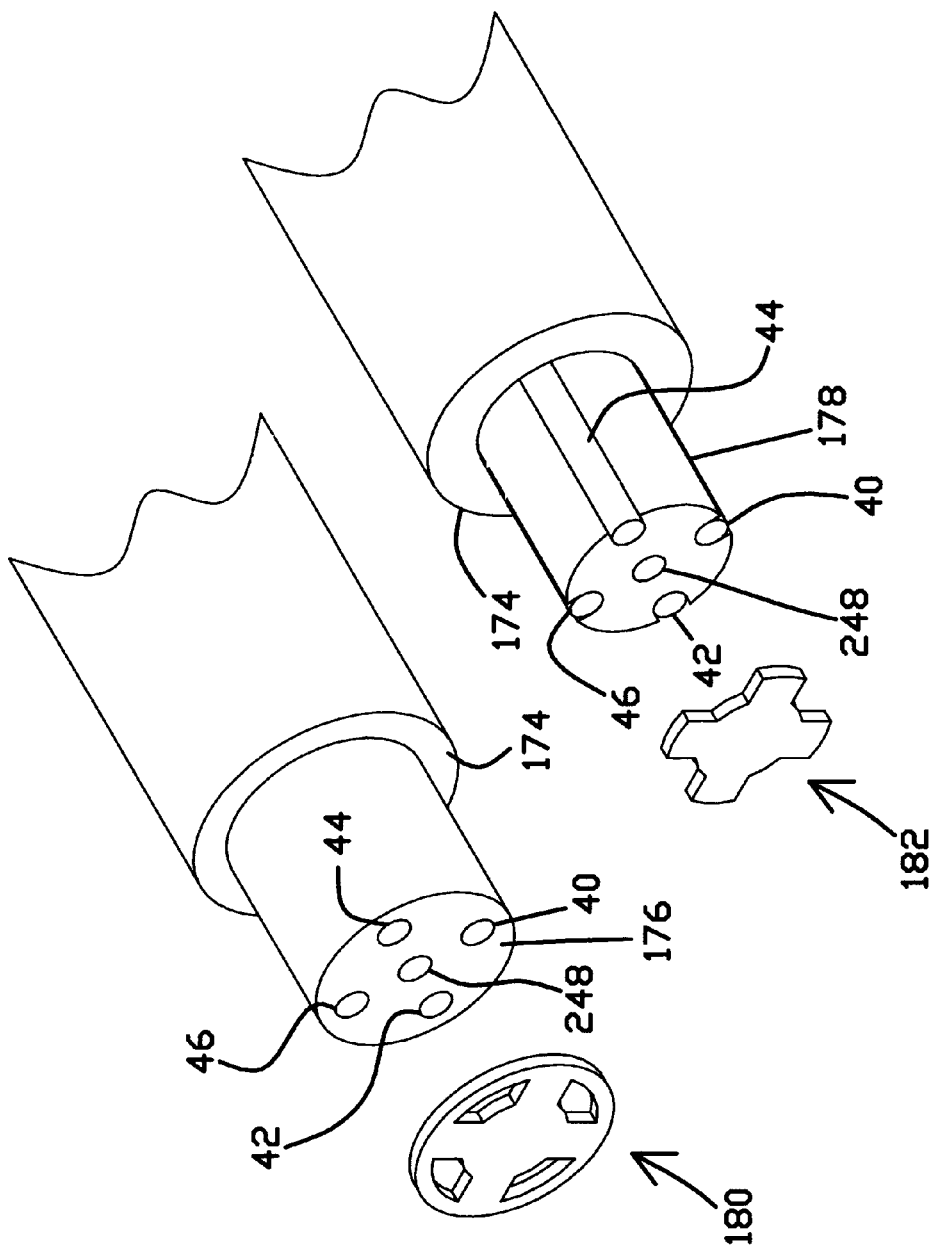
FIG. 10 is an exploded view of the embodiment of FIG. 9 showing a through hole fiber fixture, along with a second alternative embodiment for a reflector plate and side groove fiber fixture.
Figure 11:
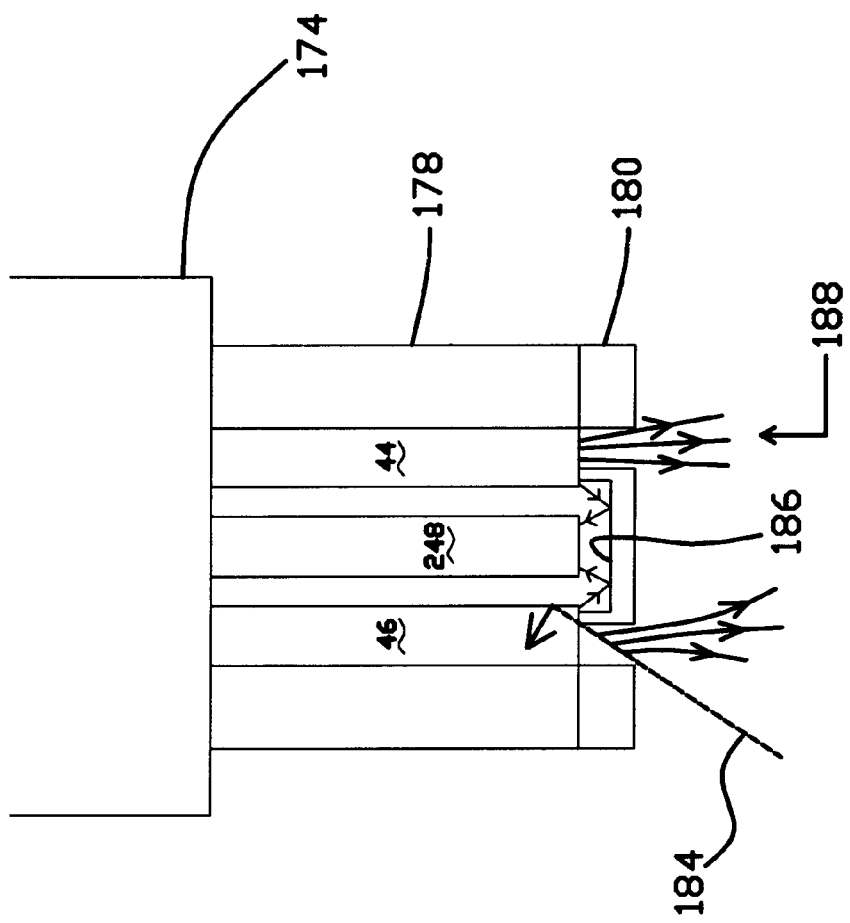
FIG. 11 is a simplified section view of the first alternative embodiment reflector plate and fiber fixture.

FIGS. 9, 10 and 11 show a first option for a reflector plate for probe tip optical fibers. A second option for the reflector plate is shown in FIG. 10. A retaining sleeve 174 surrounds a through hole fiber fixture 176 (in the first option) or a side groove fiber fixture 178 (in the second option). Reflector plate 180 is used in the first option, while reflector plate 182 is used in the second option. The 800 nm signal fiber 40, the 760 nm signal fiber 42, the 720 nm signal fiber 44, and the 680 nm signal fiber 46 surround the reference receive fiber 248. Reflector plate 180 has a concave surface in front of the reference fiber 248, as may be seen most clearly in FIG. 11. In FIG. 11, the reflector plate 180 acts as a one way light collector. Light backscattered from a measurement surface cannot enter the reference receive fiber 248 as illustrated by arrow 184 indicating light backscattered from the sample. The concave inside surface 186 reflects a portion of the emitted light back to the PMT detectors. Arrows 188 indicate light emitted to the measurement sample (tissue).

The invention offers important advantages. The LED feedback photodiodes and associated hardware of conventional prior art instruments can be removed. LED output drift is measured in combination with PMT drift with the dual optical path shutter configuration. Also, there is no need for thermal electric coolers and associated hardware for maintaining precise temperature control of the optical bench. Since there is no need for thermal electric coolers, the instrument power supply can be downsized to better match the monitor power consumption. Dual axial muffin fans can be used to provide an even forced air convection around the PMTs and optical bench to maintain the temperature of these components near ambient.

The invention is not to be taken as limited to all of the details thereof as modifications and variations thereof may be made without departing from the spirit or scope of the invention.

What is claimed is:

1. A spectrophotometric instrument; comprising:
 a source of measurement light signals having measurement light wavelengths;
 a probe having:
  a tissue-engaging surface;
  one or more send fibers coupled to the measurement light signal source for transmitting the measurement light signals to the tissue-engaging surface; and
  one or more receive fibers for receiving light including the measurement light signals after the measurement light has been transmitted through the tissue;
  reference signal optics coupled to the measurement light signal source between the measurement light signal source and the tissue-engaging surface, for transmitting a reference light signal portion of the measurement light signal;
 a detector for generating electrical signals representative of the measurement light signals and the reference light signals;
 optical paths for coupling the measurement light signal from the receive fibers and the reference light signal portion from the reference signal optics to the detector; and
 an optical path control for selectively allowing either the measurement light signal or the reference light signal portion to the detector, whereby the detector can output a reference light sample value when the reference light signal portion is coupled to the detector, and the detector can output a measurement light sample value when the measurement light signal portion is coupled to the detector.

2. The instrument of claim 1 wherein the optical paths include optics.

3. The instrument of claim 2 wherein the optics include an attenuator in the reference light signal path for reducing the portion of the reference light signal that is directed to the detector.

4. The instrument of claim 2 wherein the optics includes at least one partially transmissive mirror for folding the measurement light signal and the reference light signal into a common path.

5. The instrument of claim 1 wherein the path control includes a shutter.

6. The instrument of claim 5 and further including a motor for driving the shutter.

7. The instrument of claim 1 wherein the measurement light signal source includes a plurality of sources of narrow-bandwidth light.

8. The instrument of claim 1 wherein the reference signal optics includes an optical fiber.

9. The instrument of claim 1 wherein the reference signal optics further includes a light mixer.

10. The instrument of claim 1 wherein the reference signal optics includes a reflector.

11. The instrument of claim 1 and further including a controller for calculating corrected measurement sample signals at each measurement light wavelength as a function of a current measurement signal, a baseline reference signal and a current reference signal.

12. The instrument of claim 11 wherein the controller calculates the corrected measurement sample signals as a function of: Current Measurement ×Baseline Reference/ Current Reference.

13. The instrument of claim 11 wherein the controller calculates measurements as a function of: Log (Baseline Sample/Corrected Sample).

14. A spectrophotometric instrument, including a measurement signal optical input for receiving a measurement light signal transmitted through tissue being analyzed;

a reference signal optical input for receiving a reference light signal which is a portion of the measurement light signal that has not been transmitted through the tissue being analyzed;

a detector for generating electrical signals representative of the measurement light signals and the reference light signals;

optical paths for coupling the measurement light signal from the measurement signal optical input and for coupling the reference light signal from the reference signal optical input to the detector; and an optical path control for selectively allowing either the measurement light signal or the reference light signal to the detector, whereby the detector can output a reference light sample value when the reference light signal is coupled to the detector, and the detector can output a measurement light sample value when the measurement light signal is coupled to the detector.

15. The instrument of claim 14 and further including a controller for calculating corrected measurement values as a function of the detected measurement light signal and reference light signal.

* * * * *

UNITED STATES PATENT AND TRADEMARK OFFICE
CERTIFICATE OF CORRECTION

PATENT NO.     : 6,377,840 B1
DATED          : April 23, 2002
INVENTOR(S)    : Sergey I. Gritsenko et al.

It is certified that error appears in the above-identified patent and that said Letters Patent is hereby corrected as shown below:

<u>Title page,</u>
Item [56], References Cited, FOREIGN PATENT DOCUMENTS, please add the following:
-- EP    0 290 279 A1    11/1988
   EP    0 367 737 A2    5/1990
   GB    1 558 643       1/1980
   GB    1 386 734       3/1975 --

Signed and Sealed this

Twenty-seventh Day of April, 2004

JON W. DUDAS
*Acting Director of the United States Patent and Trademark Office*